U S010709856B2

(12) United States Patent
Feldhahn et al.

(10) Patent No.: US 10,709,856 B2
(45) Date of Patent: Jul. 14, 2020

(54) OPERATING AND INFORMATION SYSTEM FOR A BREATHING APPARATUS

(71) Applicant: WEINMANN GERAETE FUER MEDIZIN GMBH + CO. KG, Hamburg (DE)

(72) Inventors: Karl-Andreas Feldhahn, Hamburg (DE); Christof Schroeter, Karlsruhe (DE); Andreas Rensmann, Karlsruhe (DE); Uwe Strempel, Pforzheim (DE); Regina Schaefer, Iffezheim (DE); Matthias Schwaibold, Karlsruhe (DE)

(73) Assignee: LOEWENSTEIN MEDICAL TECHNOLOGY S.A., Luxembourg (LU)

(*) Notice: Subject to any disclaimer, the term of this patent is extended or adjusted under 35 U.S.C. 154(b) by 1173 days.

(21) Appl. No.: 14/914,338

(22) PCT Filed: Aug. 29, 2014

(86) PCT No.: PCT/DE2014/000453
§ 371 (c)(1),
(2) Date: Feb. 25, 2016

(87) PCT Pub. No.: WO2015/027980
PCT Pub. Date: Mar. 5, 2015

(65) Prior Publication Data
US 2016/0213869 A1 Jul. 28, 2016

(30) Foreign Application Priority Data

Aug. 29, 2013 (DE) .................. 10 2013 014 303
Mar. 28, 2014 (DE) .................. 10 2014 004 448

(51) Int. Cl.
A61M 16/00 (2006.01)
G06F 3/0484 (2013.01)
(Continued)

(52) U.S. Cl.
CPC .... *A61M 16/0051* (2013.01); *A61M 16/0057* (2013.01); *A61M 16/024* (2017.08);
(Continued)

(58) Field of Classification Search
CPC ..... G06F 3/44; G06F 3/05; G06F 3/06; G06F 3/07; G06F 3/08; G06F 3/09; G06F 3/017;
(Continued)

(56) References Cited

U.S. PATENT DOCUMENTS 5,881,723 A 3/1999 Wallace et al.
5,915,379 A 6/1999 Wallace et al.
(Continued)

FOREIGN PATENT DOCUMENTS

WO 9841267 A1 9/1998

*Primary Examiner* — Quoc A Tran
(74) *Attorney, Agent, or Firm* — Abel Schillinger, LLP

(57) ABSTRACT

The invention relates to an operating- and information system for a breathing apparatus, comprising a display for displaying information and for displaying operating fields for the user, and comprising at least one touch-sensitive input field arranged in close proximity to the displayed operating field. According to the invention, a first operating field and a second operating field are displayed in the region of the display, and a processing unit, which is coupled to the display and to the touch-sensitive input unit, is designed to register an operation of the first operating field via the touch-sensitive input unit, and, in accordance therewith, to cause the control unit to execute the function associated with the operating field.

20 Claims, 11 Drawing Sheets

(51) Int. Cl.
*G06F 3/041* (2006.01)
*G06F 3/0488* (2013.01)
*G06F 3/02* (2006.01)
*G06F 3/0482* (2013.01)
*G16H 40/63* (2018.01)
*A61M 16/10* (2006.01)
*A61M 16/16* (2006.01)
*G06F 17/00* (2019.01)

(52) U.S. Cl.
CPC .......... *A61M 16/109* (2014.02); *A61M 16/16* (2013.01); *G06F 3/02* (2013.01); *G06F 3/0412* (2013.01); *G06F 3/0482* (2013.01); *G06F 3/04842* (2013.01); *G06F 3/04847* (2013.01); *G06F 3/04883* (2013.01); *G06F 3/04886* (2013.01); *G16H 40/63* (2018.01); *A61M 2205/14* (2013.01); *A61M 2205/3386* (2013.01); *A61M 2205/505* (2013.01); *A61M 2205/52* (2013.01); *A61M 2205/587* (2013.01); *A61M 2230/40* (2013.01)

(58) Field of Classification Search
CPC ..... G06F 3/16; G06F 3/17; G06F 3/10; G06F 3/11; G06F 3/12; G06F 3/13; G06F 3/14; G06F 3/15; G06F 3/0487; G06F 3/04842; G06F 3/0484; B60K 35/00; A61M 16/0051; A61M 16/005; A61M 16/16; A61M 16/109; A61M 2205/502; A61M 2205/505

See application file for complete search history.

(56) References Cited

U.S. PATENT DOCUMENTS

| | | | |
|---|---|---|---|
| 5,915,380 A | 6/1999 | Wallace et al. | |
| 6,024,089 A | 2/2000 | Wallace et al. | |
| 6,158,432 A | 12/2000 | Biondi et al. | |
| 6,269,812 B1 | 8/2001 | Wallace et al. | |
| 6,305,373 B1 | 10/2001 | Wallace et al. | |
| 6,360,745 B1 | 3/2002 | Wallace et al. | |
| 6,369,838 B1 | 4/2002 | Wallace et al. | |
| 6,675,801 B2 | 1/2004 | Wallace et al. | |
| 7,036,504 B2 | 5/2006 | Wallace et al. | |
| 8,555,882 B2 | 10/2013 | Wallace et al. | |
| 2003/0062045 A1 | 4/2003 | Woodring et al. | |
| 2004/0118404 A1* | 6/2004 | Wallace | A61M 16/0051 128/205.23 |
| 2008/0072896 A1* | 3/2008 | Setzer | G06F 19/00 128/200.24 |
| 2011/0138308 A1 | 6/2011 | Palmer et al. | |
| 2011/0154241 A1 | 6/2011 | Skidmore et al. | |

* cited by examiner

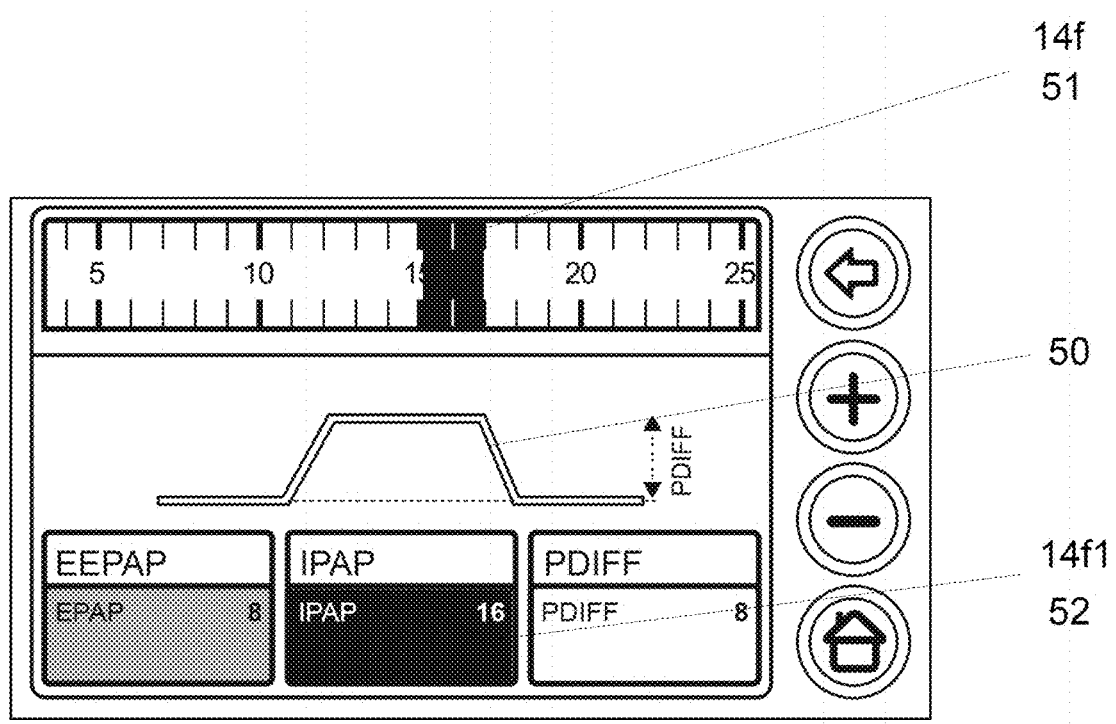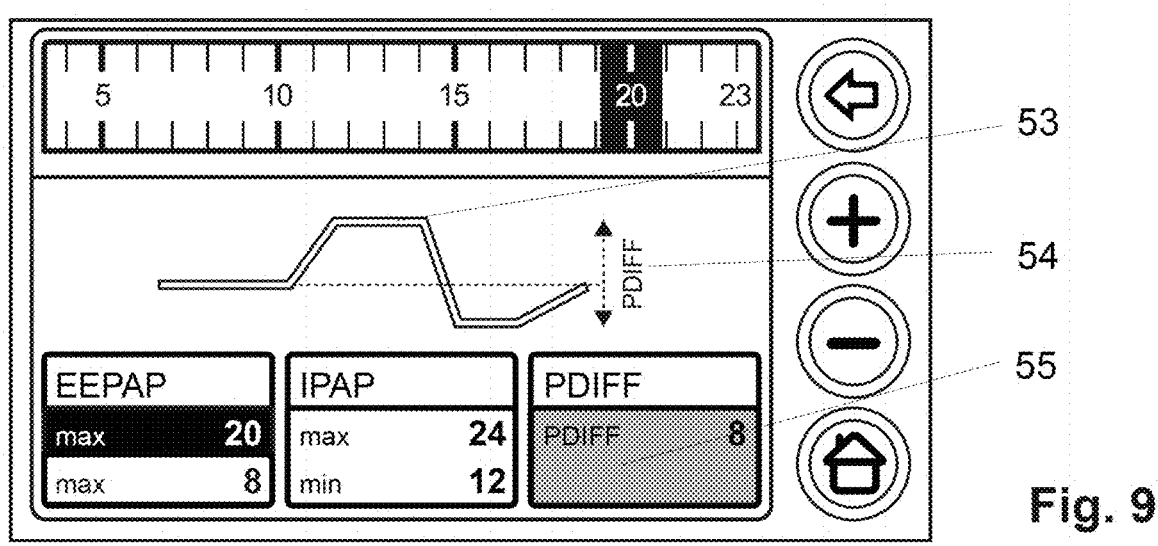
Fig. 9

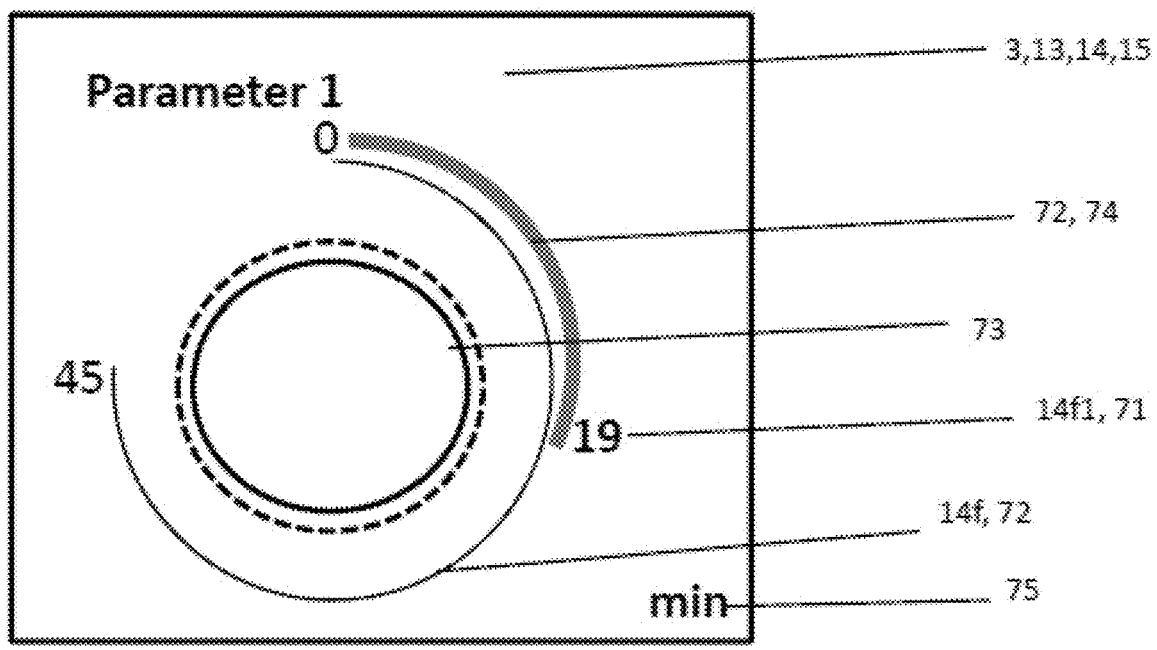
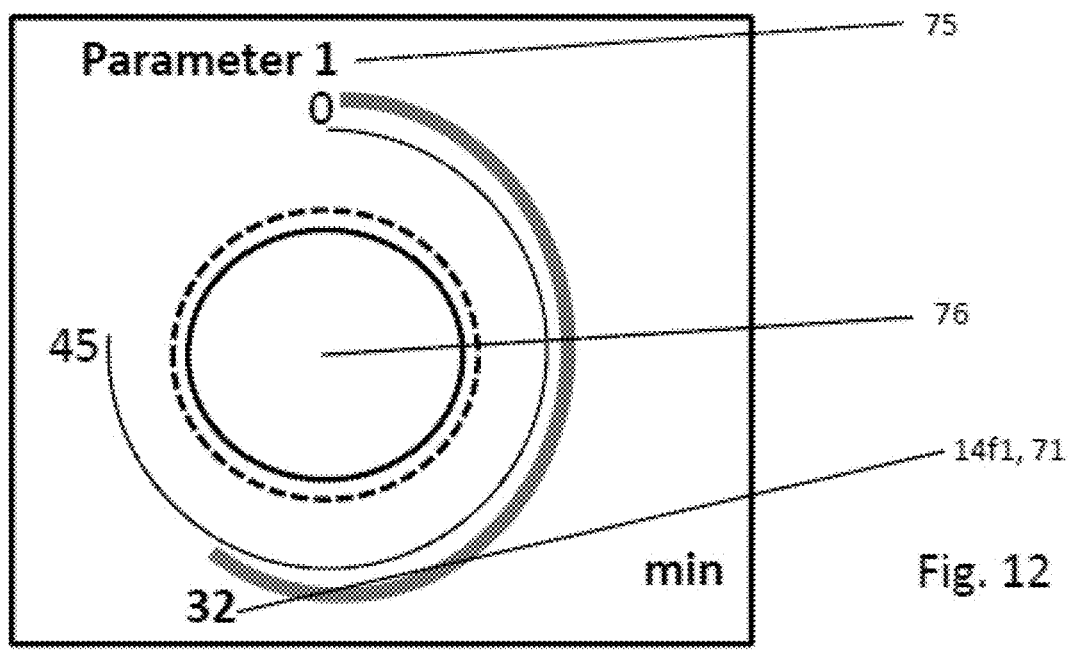
Fig. 12

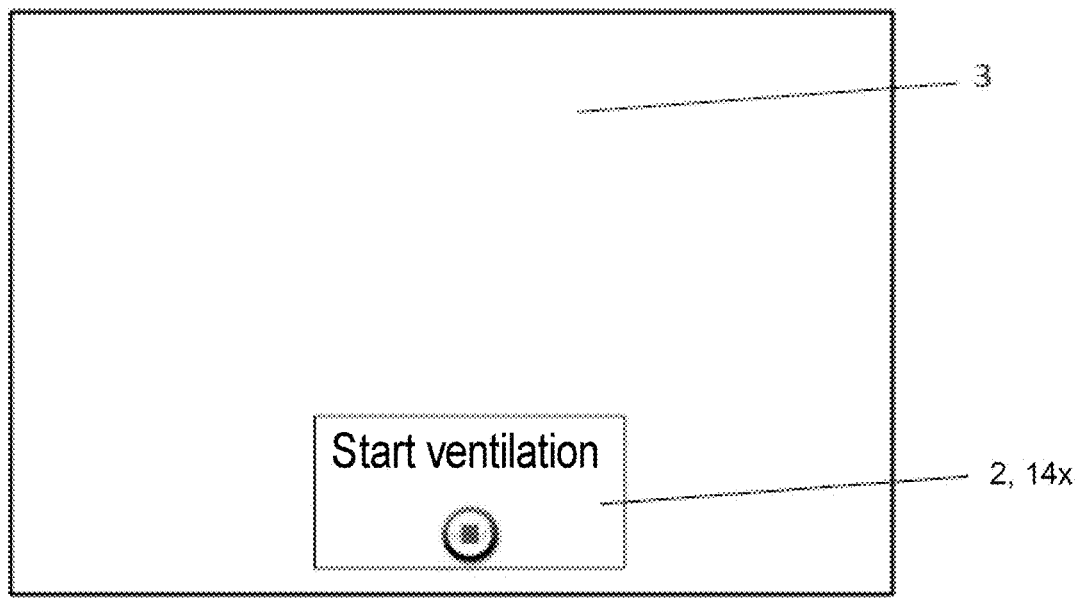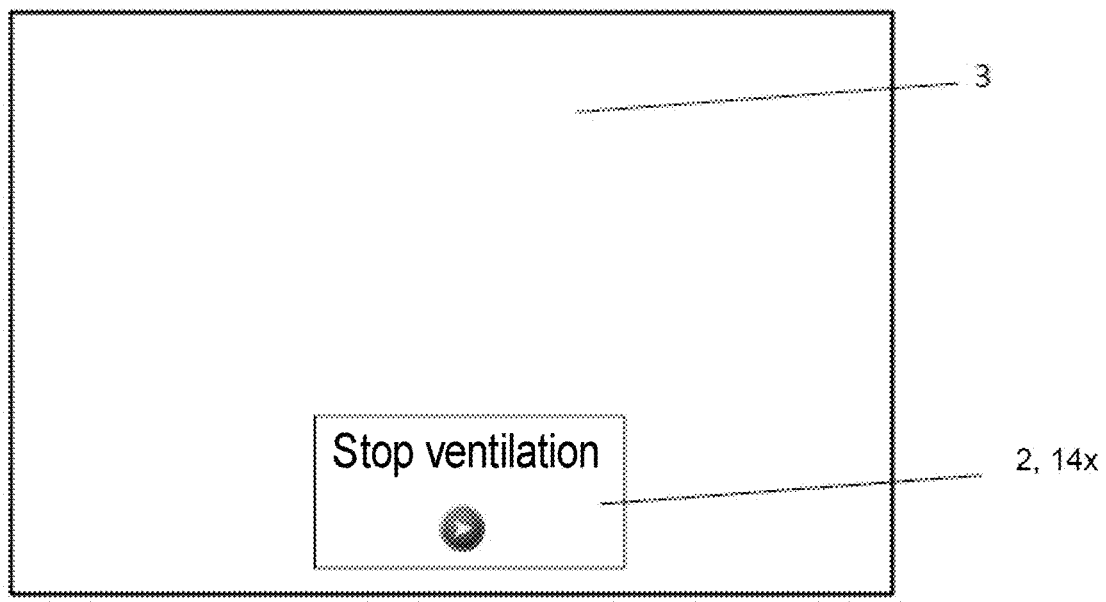
Fig.14

OPERATING AND INFORMATION SYSTEM FOR A BREATHING APPARATUS

BACKGROUND OF THE INVENTION

1. Field of the Invention

The invention relates to an operating and information system for a breathing apparatus.

2. Discussion of Background Information

Breathing apparatuses usually have separate operating and information or display elements. Operating elements are in the form of switches or rotary knobs, for example. The adjustments made using the operating elements can then be read on separate displays. This results in complex operation for the user with menu guidance which is not very intuitive.

The object of the present invention is therefore to provide a user-friendly and intuitively operable operating and information system for a breathing apparatus.

The object is achieved by means of the features of the main claim.

SUMMARY OF THE INVENTION

The operating and information system according to the invention for a breathing apparatus, preferably for a CPAP, APAP, bi-level or home therapy breathing apparatus, is equipped with a display for displaying information and for displaying operating fields for the user and with at least one touch-sensitive input field in spatial proximity to the displayed operating field,
- a first operating field and a second operating field being displayed in the region of the display,
- a processing unit which is coupled to the display and to the touch-sensitive input unit, the processing unit being configured
- to detect operation of the first operating field via the touch-sensitive input unit and, on the basis thereof, to cause the control unit to carry out or display the function assigned to the operating field.

Operation of the second operating field is preferably detected by the processing unit via the touch-sensitive input unit, the processing unit then causing the control unit to call up a context-dependent submenu, the submenu comprising a selection of actuatable adjustment functions for the menu, the control unit visualizing adjusted parameters in the region of the menu and applying them by means of control commands to an associated actuator.

A memory is assigned to the control unit and adjusted parameters or values are written to the memory by the control unit, the memory storing at least the values input and used last.

According to the invention, an undo function is provided and an undo operating field is provided for the undo function and preferably symbolizes or reproduces an arrow, and touching of the undo operating field is detected by the processing unit coupled to the touch-sensitive input unit, and the processing unit then causes the control unit to retrieve the values stored last from the memory and to visualize or use them.

Operating processes and/or apparatus outputs are preferably prioritized by the control unit. This is carried out automatically by the control unit in accordance with stored rules in such a manner that, if the control unit registers an operating process with a higher priority or an apparatus output, it at least partially superimposes the operating process with the higher priority or the apparatus outputs on an instantaneous operating field in the region of the display.

The display is preferably lit or backlit and is controlled by the control unit in such a manner that, after a defined or definable period in which the touch-sensitive input unit is not used (no touching), the control unit automatically dims the lit or backlit display or completely switches off the lighting or backlighting.

Touching of the touch-sensitive input unit is transmitted to the control unit by the processing unit in the state of dimmed lighting or backlighting or lighting or backlighting which has been completely switched off, and the control unit then lights or backlights the display again.

The control unit registers current or resistance or voltage changes in the region of the interfaces or the connections to the humidifier.

The control unit detects storage media connected via the interface and a connected storage medium is displayed as an operating field in the region of the touch-sensitive input unit and data which are extraneous to the therapy can therefore also be loaded into the breathing apparatus and/or executed by the latter.

The control unit registers current or resistance or voltage changes in the region of the interfaces or the connections to the humidifier and thus detects when a humidifier is adapted to the humidifier connection. The control unit then displays a new menu with an operating field for the humidifier via the display.

The menu for controlling the humidifier is displayed substantially at a position on the display which was previously not occupied by a menu.

Additional operating fields which are initially not active are visualized adjacent to the operating field for the humidifier, actuation of the operating field for the humidifier being detected by the processing unit which causes the control unit to activate the operating fields, and the latter being used to adjust the humidifier heating level, and the selected humidifier level then being displayed in the operating field, and the selected value also being adjusted and used by the control unit by means of a control signal to the humidifier.

The control unit registers current or resistance or voltage changes in the region of the heating element of the humidifier and therefore detects a falling or low water level on the basis of an increased current or resistance or voltage value of the heating element. This causes the control unit to display a symbol or a text message symbolizing or mentioning a low water level in the region of the display.

The operating field is preferably highlighted by means of a more intensive color, as a result of which the user is made aware of the adjustment function. Additional operating fields can be visualized in a faint color adjacent to the operating field. The fainter color makes the user aware of the fact that the fields are not active. Actuation of the operating field is detected by the processing unit which causes the control unit to visualize the additional operating fields in an intensive color. In addition, + and − symbols can now be visualized and are used to adjust the humidifier heating level.

The selected humidifier level is then displayed in the operating field and the amended value is additionally set and used by the control unit by means of a control signal to the humidifier. In the case of the humidifier, the heating unit of the humidifier is heated with a choice of a higher heating level.

According to the invention, an operating area or an operating element is always provided (basic state), the actuation of which causes the operating and information system to display the basic state via the control unit. For this purpose, active operating fields or other contents are hidden.

According to the invention, an operating area or an operating element is provided for each adjustment situation (undo), the actuation of which causes the operating and information system to restore the previously active state via the control unit. For this purpose, instantaneous adjustments and display options are stored by the control unit in a retrievable manner and are activated again in response to actuation of the undo operating area.

The invention provides for an active operating field to be highlighted by means of a more intensive color, as a result of which the user is made aware of the adjustment function and operating fields which are not active are visualized in a faint color. The fainter color makes the user aware of the fact that the fields are not active.

The apparatus according to the invention communicates with the operator using a wide variety of mainly optical feedback. With regard to possible usage errors, self-control of the operator is possible by means of key feedback, for example. This increases safety when handling the apparatus and reduces the hazards caused by incorrect adjustments.

Forms of Feedback:

Symbols for success. The mask denseness is visualized using green squares. The usage duration is visualized using green hearts if it is within the specifications. If the usage duration is too short, the usage duration is visualized in orange or red in a graduated manner.

Color scheme display. Set values are displayed in white or black. Measured values which are in the defined range are displayed in green. Critical values are displayed in red. Warnings are displayed in orange.

Flashing feedback. An active process which has not yet been concluded, for example the storage of data or the remote transmission of data, is visualized by means of flashing.

BRIEF DESCRIPTION OF THE DRAWINGS

Exemplary embodiments of the invention are schematically illustrated in the drawings, in which:

FIG. 9 shows a graphical adjustment aid for at least one pressure, FIG. 12 shows a schematic illustration of a circular operating element, FIG. 14 shows an embodiment wherein a (start/stop) operating area or a mechanical (start/stop) operating element is provided on the touchscreen.

DETAILED DESCRIPTION OF EMBODIMENTS

Figure 1:
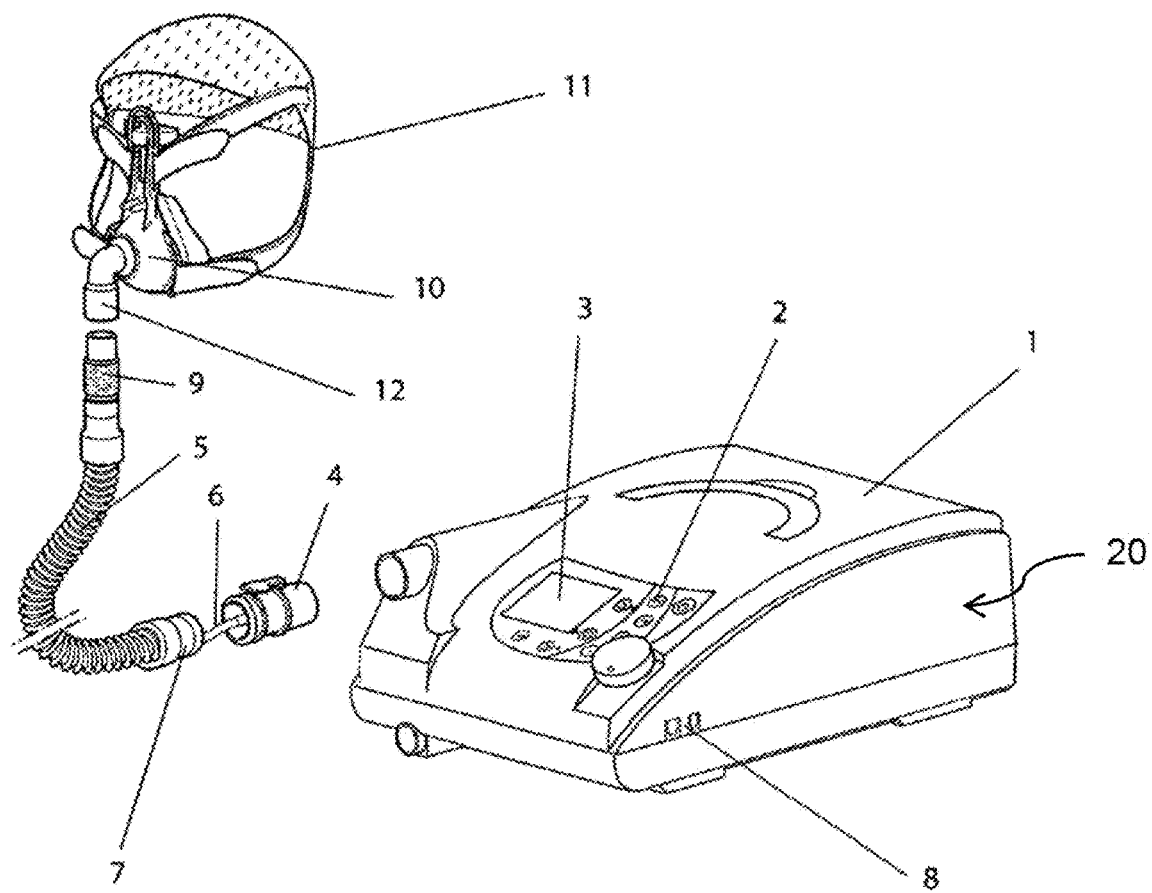
FIG. 1 shows a perspective illustration of a breathing apparatus with a breathing mask and a respiratory gas hose.

FIG. 1 shows the fundamental structure of a breathing device. An operating element (2) and an operating and information system (3) consisting of a display (13) and a touch-sensitive input unit (15) with at least one operating field (14) are arranged in the region of an apparatus housing (1) of the breathing apparatus (20) having a respiratory gas source in the interior of the apparatus. A connecting hose (5) is connected via a coupling (4). An additional pressure-measuring hose (6) which can be connected to the apparatus housing (1) via a pressure inlet connection piece (7) can run along the connecting hose (5). In order to make it possible to transmit data, the apparatus housing (1) has at least one interface (8). A humidifier (30) can also be adapted.

An exhalation element (9) is arranged in the region of an extent of the connecting hose (5) which faces away from the apparatus housing (1). An exhalation valve may likewise be used.

FIG. 1 also shows a patient interface which is in the form of a respiratory mask (10) and is implemented as a nasal mask. Fixing in the region of a patient's head can be carried out using a head cover (11). In the region of its extent facing the connecting hose (5), the patient interface (10) has a coupling element (12).

Data, for example dead space volume, can be input and/or output via the interface (8). The interfaces may be wired, in the form of an infrared interface, in the form of a Bluetooth interface or in the form of a USB. A card slot is preferably also provided. The interface (8) may also be in the form of a LAN interface or another interface for connection to the Internet. An oxygen connection valve can be adapted for the breathing device in the region of an apparatus housing. It is conceivable for the respiratory gas to additionally be enriched with oxygen in order to improve patient care.

Data which are extraneous to the therapy can also be loaded into the breathing apparatus according to the invention via the interface (8)—for example in the form of a card slot or USB—and can be executed by said apparatus. The idea is thus to display photos or videos, for example, in the region of the display by means of storage media via the interface (8). If external storage media are detected by the apparatus, the user must confirm an enquiry in the operating field, whereupon the data are either stored in the region of the breathing apparatus or are executed.

The breathing apparatus (20) according to the invention is designed in such a manner that it can be connected to a patient via a hose and a patient interface in order to provide ventilation. It comprises a source for respiratory gas, which is in the form of an electric motor with an impeller for example, and a device for determining pressure and/or flow and/or volume of the respiratory gas as well as a control unit (19) which is designed in such a manner that it determines a respiratory gas pressure for each breathing cycle on the basis of a predetermined value for the patient and/or on the basis of measurement signals for the pressure and/or flow and/or volume parameters and regulates the respiratory gas source in such a manner that the respiratory gas pressure is produced.

The control unit (19) is also designed in such a manner that it determines the instantaneous pressure and/or flow and/or volume of respiratory gas and displays the instantaneous value using the operating and information system (3)

to the control unit. The control unit (19) is also designed in such a manner that it determines trend changes in its calculations over time based on one or more parameters, the trend changes being able to be displayed on the display.

The control unit (19) also compares those parameter values which have been specified by a user, for example upper and lower pressure limits or a maximum tolerable number of apnea per unit time or a maximum tolerable leakage, with the instantaneous values and generates an item of user information relating to deviations from the specification. The user information is preferably graphically visualized via the operating and information system (3).

Apnea and hypopnea are therefore identified from the measured respiratory flow by means of a decrease in the breathing (time) volume for a period of at least 10 s. Snoring is additionally identified via pressure and flow fluctuations, and flattening is identified via the inspiratory flow contour. Indices are calculated therefrom for each sufficiently long nighttime therapy, namely: AHI (=number of apnea+hypopnea for each artifact-free therapy duration), RDI (=number of all respiratory events for each artifact-free therapy duration), proportion of breaths with flattening, proportion of breaths with snoring. Data which allow deductions to be made about the usage behavior or the usage duration of the apparatus by the patient are preferably also determined. These data are determined and stored on a daily or weekly or monthly basis. If necessary, the usage data are retrieved and transmitted, possibly together with an apparatus identifier, via an Internet connection or a mobile radio connection.

Figure 2:
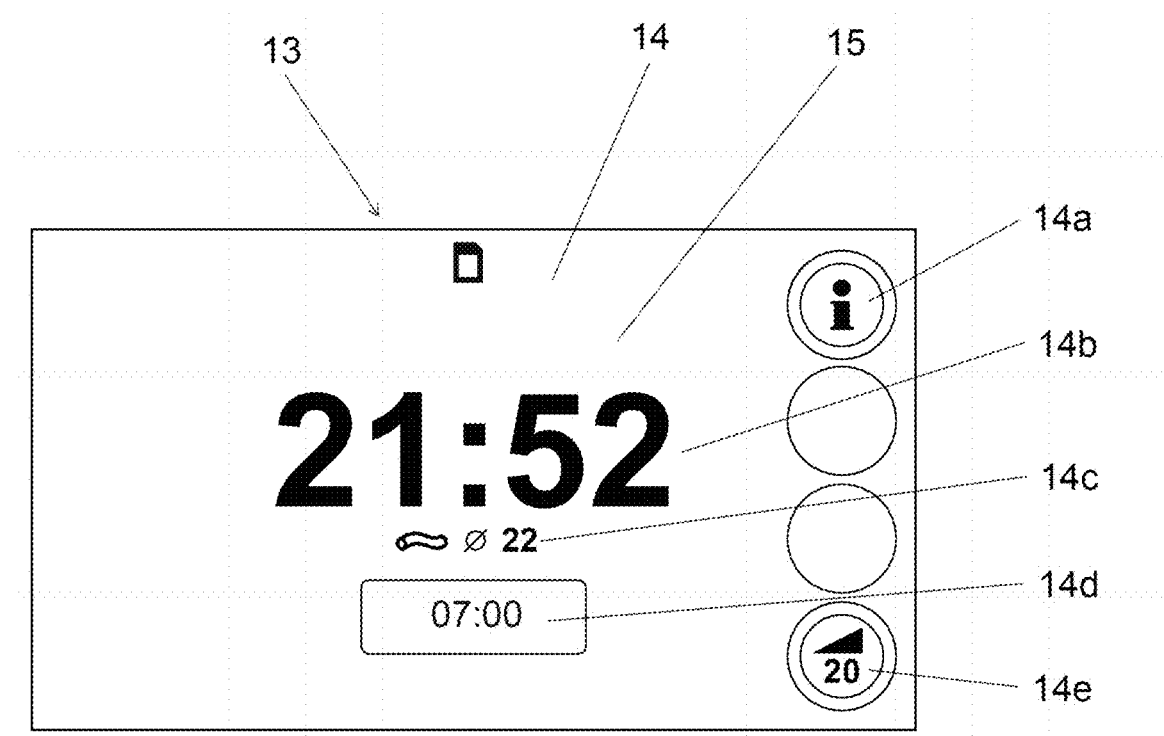
FIG. 2 shows a display of the operating and information system.

FIG. 2 shows the operating and information system (3) for a breathing apparatus (20) with a lit or backlit display (13) for displaying operating fields (14) or information for the user and with a touch-sensitive input unit (15) in spatial proximity to the displayed operating field (14). In a specific embodiment, it is a man-machine interface in the form of a so-called touchscreen, in which case a person skilled in the art knows different types which are all possible as part of the operating and information system (3) according to the invention. At least one first operating field (14a) and one second operating field (14b) are displayed in the region of the display. The control unit (19) is configured to display the menu on the display (13).

A processing unit (18) which is coupled to the display (13) and to the touch-sensitive input unit (15) is configured to detect operation of the operating field (14) via the input unit (15) and, on the basis thereof, to control a function of the menu via the control unit (19). A menu assigned to an operating field (14b, 14c, 14d . . . ) is preferably displayed on the display (13) in a manner spatially adjacent to the operating field or at the same position of the operating field. Simultaneous or time-delayed operation of further operating fields (14b, 14c, 14d . . . ) via the input unit (15) can likewise be detected via the processing unit (18). The processing unit then causes the control unit (19) to call up the menu assigned to the selected operating field in the first level (=submenu). A submenu assigned to an operating field (14b, 14c, 14d . . . ) is preferably displayed on the display (13) in a manner spatially adjacent to the operating field or to the menu or at the same position of the operating field/menu.

A submenu is displayed by the control unit (19) via the display (13). The submenu is preferably displayed substantially at the same position as the menu from which the submenu emerges. Further operating fields (14) or information can now be displayed in the submenu. Navigation in a plurality of submenus is fundamentally provided; however, the branch is preferably no deeper than two menu levels. In order to return to the menu again from a submenu, an operating field (14) is always provided at the same position, the actuation of which field causes the control unit to display the menu of the next higher hierarchical level on the display (13).

The control unit also has a clock which determines the time and displays it in the region of the display. A wake-up time/alarm time with a signaling device is also coupled thereto. The user can predetermine a time, upon the reaching of which an acoustic and/or optical alarm is output via the signaling device.

In the basic display, the display (13) centrally shows the instantaneous time. The wake-up time which has been input is optionally displayed underneath. The time and wake-up time can be set by touching the respectively assigned operating fields (14b, 14d). The operating fields are preferably at the position at which the time and the wake-up time are also displayed.

The average therapy pressure is displayed between the time and the wake-up time. In addition, an operating field (14c) is also provided at this position and is used to get to the submenu relating to the average therapy pressure.

The currently set ventilation pressure in hPa, with an associated operating field (14e), is displayed in the lower right-hand corner. An information field with an associated operating field (14a) is displayed in the upper right-hand corner.

Figure 3:
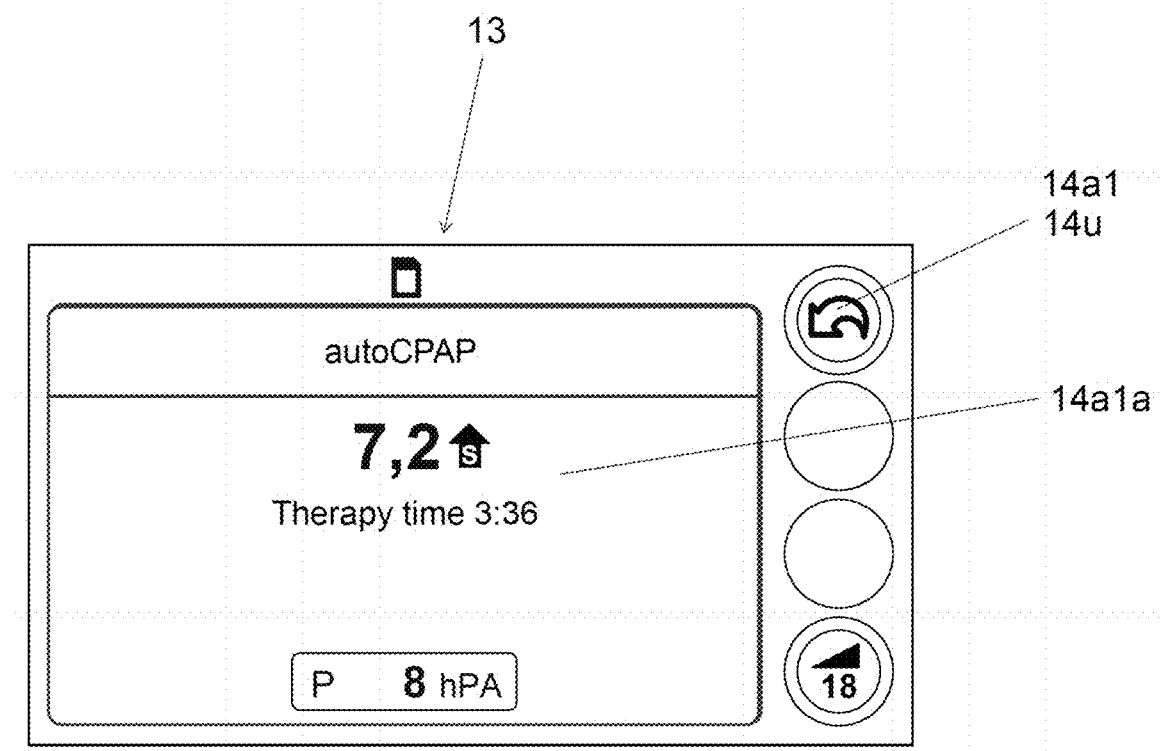
FIG. 3 shows a display for illustrating a submenu.

FIG. 3 illustrates the submenu for the operating field (14a=information field). Actuation of the information field (14a) is detected by the processing unit (18). The processing unit then causes the control unit (19) to call up and display the menu (information menu) assigned to the information field (14a). The display is preferably effected centrally in the region of the display (3), the display of the clock (14b) and the wake-up time (14d) being hidden at the same time. The information menu (14a2) is displayed in a time-controlled manner. After a number of seconds, the control unit (19) changes back to the basic display again, for example after five seconds. For this purpose, the control unit (19) has a countdown unit which counts the five seconds and then causes the control unit to activate the basic display with the clock and the wake-up time again.

The time-controlled return to the basic display is preferably provided for each menu if an input is not made within 10 seconds, for example. While the information menu has been called up, a new menu function (14a1) is particularly preferably displayed in the region of the information field (14a) in a manner ready for retrieval. In the present case, the back function (14a1) is displayed in the form of an arrow, the actuation of which ends the display of the information menu and activates the display of the basic display. In principle, an undo function is provided according to the invention for each menu function in which settings can be changed. An undo operating field (14u) which symbolizes or reproduces an arrow is provided for the undo function. Touching of the undo operating field (14u) is detected by the processing unit (18) coupled to the display (13) and to the touch-sensitive input unit (15). The processing unit (18) then causes the control unit (19) to retrieve the previous values from the memory and to display them. Touching of the field in which the values are visualized causes the control unit to also use these values.

Values relating to the progression of the therapy, namely AHI, compliance, usage duration, leakage and optionally further values, for example, are displayed in the region of the information menu (14a2). Choosing the displayed values opens a new submenu which illustrates further details and adjustment options for the displayed value.

In principle, provision is made for actuatable adjustment functions—such as the humidifier level, the therapy pressure, the time, the wake-up time or other functions—to be graphically highlighted, for example by means of a different color or a different intensity of the color, so that the user immediately recognizes which displayed information can be adjusted. The currently set value is additionally visualized in the field of the actuatable adjustment functions. If the user selects such an actuatable adjustment function, the control unit displays an additional associated menu field—the operating field—on the display and adjacent to the selected actuatable adjustment function. In the simplest case, two operating fields in the form of + and symbols are visualized above and below or to the right and to the left of the selected actuatable adjustment function. Actuation of the operating fields is detected by the processing unit (18) which then causes the control unit (19) to change the value of the actuatable adjustment functions in accordance with the input and to visualize it in the region of the display (3). In this case, provision is made for the control unit to not only visualize the value but also to cause the associated actuator to adapt or use the value by means of a control command. The set value and the actual value are preferably initially visualized and, after the actual value corresponds to the set value, only the actual value is displayed.

If, for example, the ventilation pressure—as actuatable adjustment functions—is intended to be changed, the user simply touches the corresponding field of the display in which the information relating to the instantaneous pressure is displayed, here (14e). The control unit then causes an operating field (14e1) to be displayed. The operating field may be a keyboard which is similar to a computer and is visualized in a superimposed window. The user can input the new value for the selected parameter on this keyboard. After the desired parameter has been input, the user confirms the value by means of a displayed ENTER symbol, whereupon the computer display disappears again. In the simplest case, two operating fields in the form of + and − symbols are visualized above and below or to the right and left of the selected actuatable adjustment function. Actuation of the operating fields is detected by the processing unit (18) which then causes the control unit (19) to change the value of the actuatable adjustment functions in accordance with the input and to visualize it in the region of the display. The changed parameter is displayed by the control unit in the corresponding field of the display and is set and used as the new parameter at the same time or only after user selection by means of a control signal to the blower of the breathing apparatus. The set value and the actual value are preferably initially visualized and, after the actual value corresponds to the set value, only the actual value is displayed.

The parameters which have been adjusted in this manner are simultaneously written by the control unit (19) to a memory which is used as a buffer for the parameter values to be currently used. The memory always stores at least the values input and used last. If the undo function is actuated, the memory always outputs these last values first.

Figure 4:
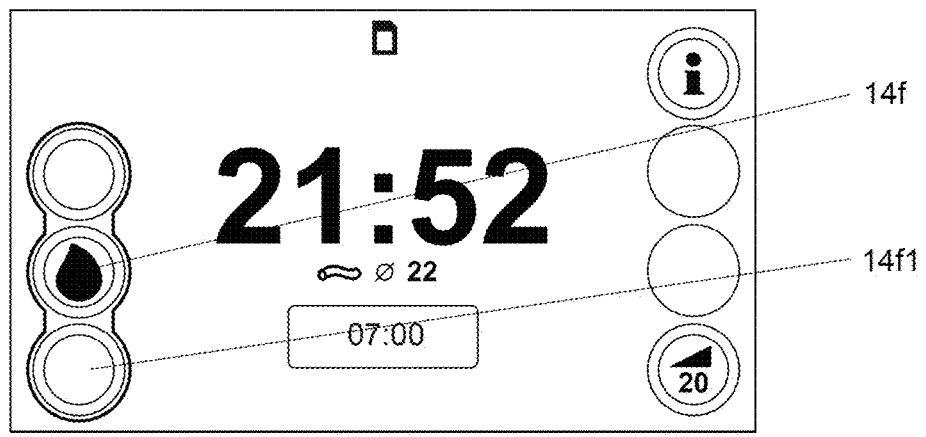
FIG. 4 shows a display for illustrating how the operating and information system detects and controls a connected humidifier.
Figure 5:
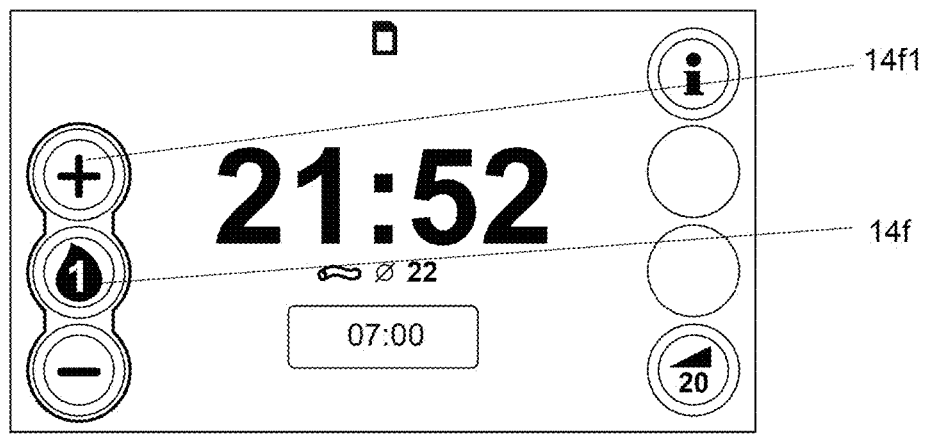
FIG. 5 shows an illustration similar to FIG. 4 in another operating state.
Figure 6:
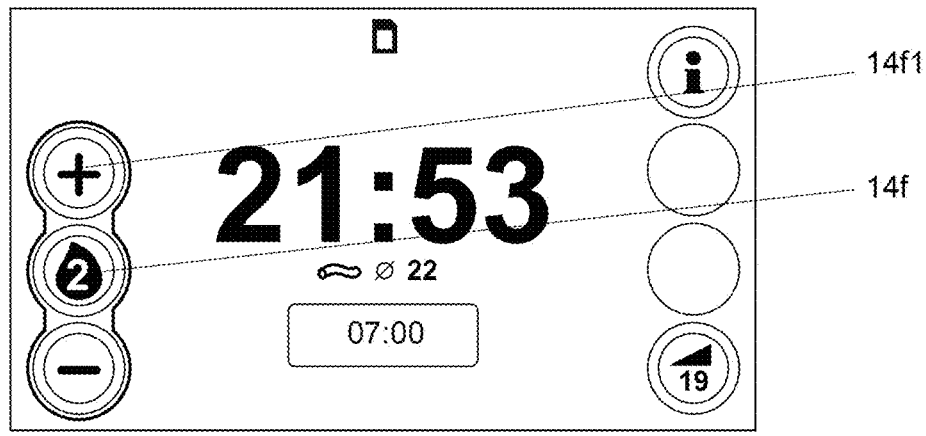
FIG. 6 shows an illustration similar to FIG. 4 and FIG. 5 for illustrating a further operating state.

FIGS. 4 to 6 now illustrate how a connected humidifier (30) is detected and controlled via the operating and information system according to the invention. The control unit (19) registers current or resistance or voltage changes in the region of the interfaces or the connections to the humidifier. If a humidifier (30) is now adapted for the humidifier connection, this is registered by the control unit (19). The control unit then displays a new menu with an operating field for the humidifier (14f) via the display (13). The menu for controlling the humidifier is preferably displayed substantially at a position on the display which was previously not occupied by a menu.

The operating field (14f) is highlighted by means of a more intensive color, as a result of which the user is made aware of the adjustment function. Two operating fields (14/1) are additionally visualized in a faint color adjacent to the operating field (14f). The fainter color makes the user aware of the fact that the fields are not active. Actuation of the operating field (14f) is detected by the processing unit which causes the control unit to visualize the two operating fields (14/1) in an intensive color. In addition, + and − symbols are now visualized. The latter are used to adjust the humidifier level. The selected humidifier level is then displayed in the operating field (14f) and the changed value is additionally set and used by the control unit (19) by means of a control signal to the humidifier (30). In the case of the humidifier, the heating unit of the humidifier is heated with a choice of a higher heating level.

The control unit (19) registers current or resistance or voltage changes in the region of the heating element of the humidifier. The resistance of the heating element increases with a falling water level. This is detected by the control unit. The control unit then displays a symbol for a low water level in the region of the display or outputs a corresponding text message.

In principle, provision is made for operation of a second operating field to be detected by the processing unit (18) via the touch-sensitive input unit and for the control unit (19) to then be caused to call up a context-dependent submenu, for example in the form of additional operating fields, the submenu comprising a selection of actuatable adjustment functions, for example in the form of plus and minus keys to adapt a set value, for the menu, and the control unit (19) visualizing parameters which have been adjusted in the region of the menu and applying them by means of control commands to an associated actuator.

In principle, provision is made for operating processes and apparatus outputs to be prioritized. This is automatically carried out by the control unit in accordance with stored rules. If, for example, an operating process with a higher priority or an apparatus output such as a warning becomes active, the operating process with the higher priority or the apparatus outputs is/are superimposed on an instantaneous operating field (14x). In this case, the control unit places the operating field (14y) assigned to the higher-priority operating process or to the apparatus output in the foreground directly in the region of the display (13) and the instantaneous operating field (14x) moves into the background.

The lit or backlit display (13) for displaying operating fields (14) or information for the user in the region of the touch-sensitive input unit (15) is controlled by the control unit (19) in such a manner that, after a defined or definable period in which the touch-sensitive input unit (15) is not used (no touching), the control unit (19) automatically dims the lit or backlit display (13) or completely switches off the lighting or backlighting. In addition, the lighting or backlighting can be adjusted by the user in a plurality of levels using a menu, with the result that the user can select a brightness level and/or color which is comfortable for him. As soon as the touch-sensitive input unit (15) is touched, the control unit switches the lighting or backlighting on again.

The control unit (19) of the operating and information system according to the invention registers current or resistance or voltage changes in the region of the interfaces or the connections to the humidifier. If a memory card or a USB stick is now inserted into the corresponding interface, this is registered by the control unit (19). The control unit then displays a new menu with an operating field for the storage medium (14s) via the display (13). The menu for the storage medium (14s) is preferably displayed substantially at a position on the display which was previously not occupied by a menu.

Alternatively, the idea is also to display the menu (14s) centrally in the region of the display. The associated operating field (14s1) is displayed adjacent to the menu and is highlighted, for example, by means of a more intensive color, as a result of which the user is made aware of the adjustment function. Actuation of the operating field (14s1) is detected by the processing unit (18) which causes the control unit (19) to display or execute the contents of the storage medium. The idea of the invention is to allow photos or videos to be displayed on the display using a USB stick or a memory card. For this purpose, the associated operating field (14s1) queries whether the photos or videos are intended to be displayed.

Touching of the operating field (14s1) is detected by the processing unit (18) which causes the control unit (19) to hide all information or menus previously displayed in the region of the display and to display the photos or videos from the storage medium in a substantially extensive manner in the region of the display. Photos are preferably automatically sequentially displayed with a selectable display time.

If alarms are produced while displaying the photos, these alarms are given a higher priority by the control unit (19) and are displayed instead of the photos. If the user wishes to check or adjust functions of the breathing apparatus or of the humidifier, he touches the touch-sensitive input unit (15) at any desired position during photo display. The processing unit (18) detects this and causes the control unit (19) to hide the photo display and to display the basic display of the breathing apparatus according to FIG. 2. After the desired adjustments have been made by the user, the control unit (19) automatically changes back to the display of the photos again.

According to the invention, a doctor and a patient menu are provided. The doctor menu provides all important adjustment options, while the patient menu provides only reduced adjustment options. For this purpose, an enable function for the doctor is provided. In order to enable the doctor menu, the doctor must input an identifier, for example, or must be authenticated using a chip card. Only then are all adjustment options enabled. Certain operating elements are activated and visible only when successful authentication has been carried out, for example those relating to the management of alarms: activation/deactivation, confirmation/acknowledgement, choice of the alarm threshold value.

The patient is not made insecure by operating elements which, although visible to him, are blocked. Information and adjustment options extraneous to the therapy are preferably displayed in the patient menu in the basic state. The time and wake-up time are therefore displayed centrally in the region of the display. Information relevant to the therapy—visualization and control of breathing parameters—is preferably displayed in the region of the display in the doctor menu, preferably at the same position as the time and wake-up time in the patient menu.

Example of a Ramp Function:

The ramp function initially provides the patient with a lower pressure than the therapy pressure, which pressure is raised to the therapy pressure in the course of minutes. The advantage for the patient is that it is easier to fall asleep. If the patient wakes up during the night and would then like to fall asleep again with the ramp function, he can initiate the ramp function according to the invention by touching the operating and information system according to the invention. This can preferably be carried out while dozing or with poor visibility in darkness or without glasses by virtue of the fact that the operating and information system according to the invention enlarges or positions the operating area (14) for the ramp function in such a manner that it is preferably always activated when the operating and information system is touched. For this purpose, the ramp function is activated by the control unit in a time-controlled manner whenever it has been determined that the operating and information system has not been used for a defined period. In contrast, in other operating situations while the patient is awake, the ramp function does not have any significance whatsoever.

The button is then hidden again or reduced and more important functions move to the foreground.

Depending on the type of parameter, another adjustment principle is useful. The operating and information system (3) according to the invention makes it possible to provide the most efficient adjustment option for each parameter. For example, the operating field may be in the form of a number block and/or a letter block in order to input numerical codes, IP addresses, the date, serial number or letters. The operating field may be in the form of a +/− field or a level display for the purpose of adjusting parameters with few defined adjustment levels.

An operating field in the form of a number line may be effected for the purpose of adjusting parameters with a large number of adjustment levels, for example the ventilation pressure or the background frequency of 6-40 1/min.

An operating field in the form of a list selection is displayed when adjusting a large number of options, for example for selecting the language for the user interface. In this case, the options which can be selected are displayed in written form in a list and the desired option is selected by touching the latter, whereupon the control unit causes the selection to be implemented by means of a control signal.

An operating field in the form of scroll keys is used to change over entire screen contents. For this purpose, operating areas with arrow symbols, for example, are displayed on the right and left in the operating and information system, the touching of which operating areas causes the control unit to display the next screen contents by means of a control signal.

According to the invention, an operating area (14g) or an operating element (2) is always provided (basic state), the actuation of which causes the operating and information system (3) to display the basic state via the control unit. For this purpose, active operating fields (14) or other contents are hidden.

According to the invention, an operating area (14u) or an operating element (2) is provided for each adjustment situation (undo), the actuation of which causes the operating and information system (3) to restore the previously active state via the control unit. For this purpose, instantaneous settings and display options are stored by the control unit in a retrievable manner and are activated again in response to actuation of the undo operating area.

The invention provides for an active operating field (14) to be highlighted by means of a more intensive color, as a result of which the user is made aware of the adjustment function, and operating fields which are not active are visualized in a faint color. The fainter color makes the user aware of the fact that the fields are not active.

Figure 7:
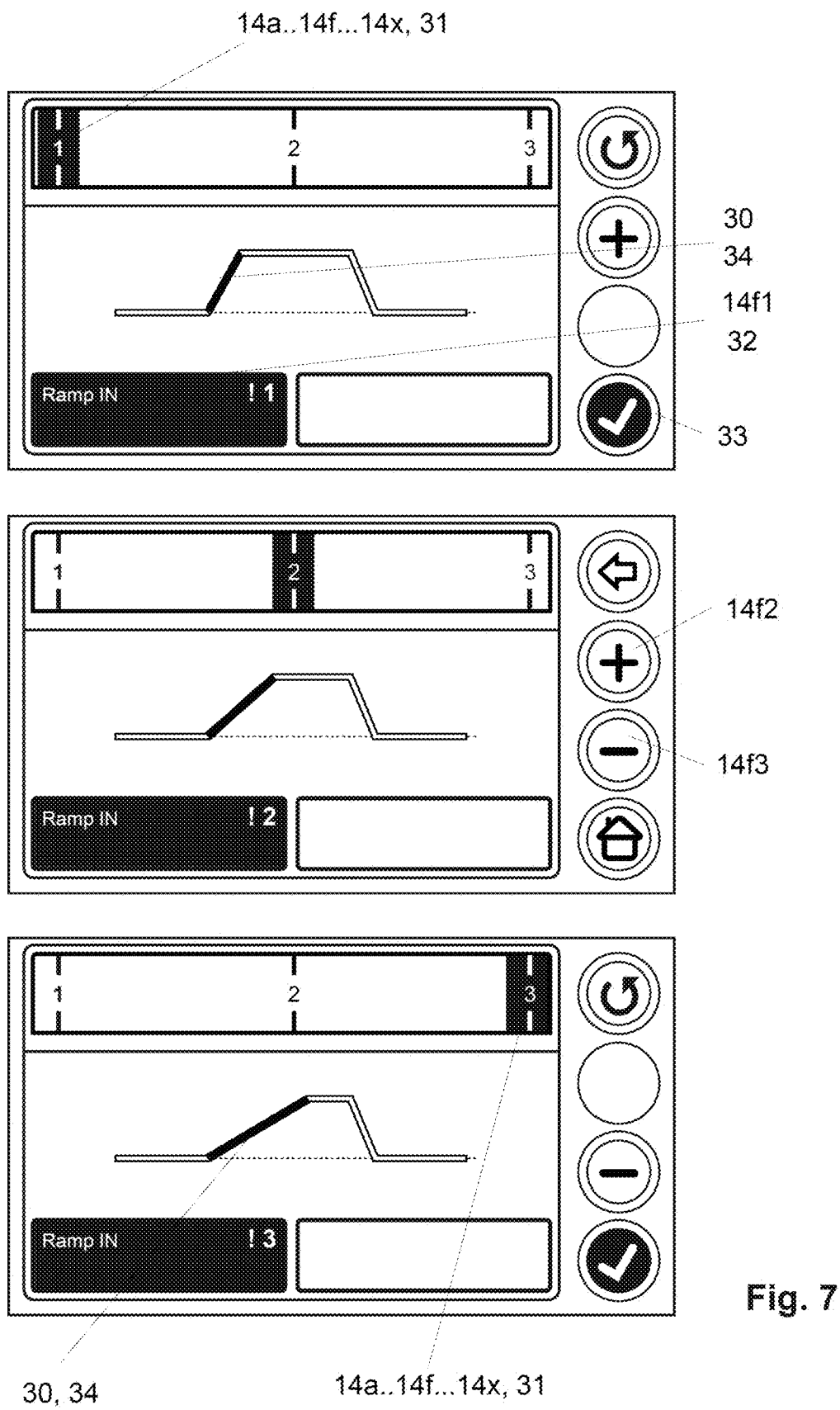
FIG. 7 shows a schematic illustration of a graphical adjustment aid for a ramp gradient.

FIG. 7 shows the graphical adjustment aid for the ramp gradient for the transition from expiratory pressure to inspiratory pressure (marked in green). The instantaneous level can be adjusted using a slider/ruler or alternatively with + and −. With its green marking, the ruler is additionally used not only as an adjustment tool but also as a display element. This provides the advantage that inexperienced users are also directly provided with a display of the value during adjustment.

In the example illustrated, it can be seen that the graphical adjustment aid provides the user with at least double feedback (31, 34), preferably triple feedback with respect to the adjustment (31, 32, 34). The operating device for a breathing apparatus comprises a touch-sensitive graphical display (3, 13, 14, 15) which at least occasionally represents the range of values for a breathing parameter (14a . . . 14x), here the ramp gradient (30), and numerically displays (31) at least individual values of the ramp gradient. In addition, a memory (21) for the value of the ramp gradient for at least one data point associated with the range of values and at least one position (14a . . . 14x) on the touch-sensitive graphical display which is associated with the data point using switching logic are used. Switching logic (18) which, when the position on the touch-sensitive graphical display which is associated with the data point using switching logic is touched, causes at least one numerical value (32) associated with the data point and/or a confirmation field (33) for the numerical value to be displayed and switching logic (18) which, when the numerical value (32) or the confirmation field (33) is touched, applies this numerical value to the associated respiratory gas parameter and writes this numerical value, with the associated respiratory gas parameter, to the memory (21) are also provided.

The operating field is in the form of a number line or ruler and the entire range of values is visualized on the display (13) in the form of a number line or bar and the visualized number line is also in the form of an operating field (14f). The operating field is touch-sensitive over the entire visualized adjustment range and the desired value can be selected by only touching the desired range.

Finger pressure or touching inside the ruler is evaluated with respect to its position in such a manner that it is not necessary to strike precisely one of the numbers 1, 2, 3, but rather the finger pressure is assigned to the closest number. The detected value (32) is visualized in an additional field (14/1). The detected value can additionally be adjusted using the symbols +/− (14/2, 14/3).

Not only individual values of the ramp gradient are preferably numerically displayed (31), but the selected value of the ramp gradient is also numerically displayed (33) and the selected ramp gradient (34) is also graphically visualized.

Alternatively or additionally, as stated with respect to FIG. 7, the ramp can also be adjusted from the inspiratory to the expiratory pressure.

Figure 8:
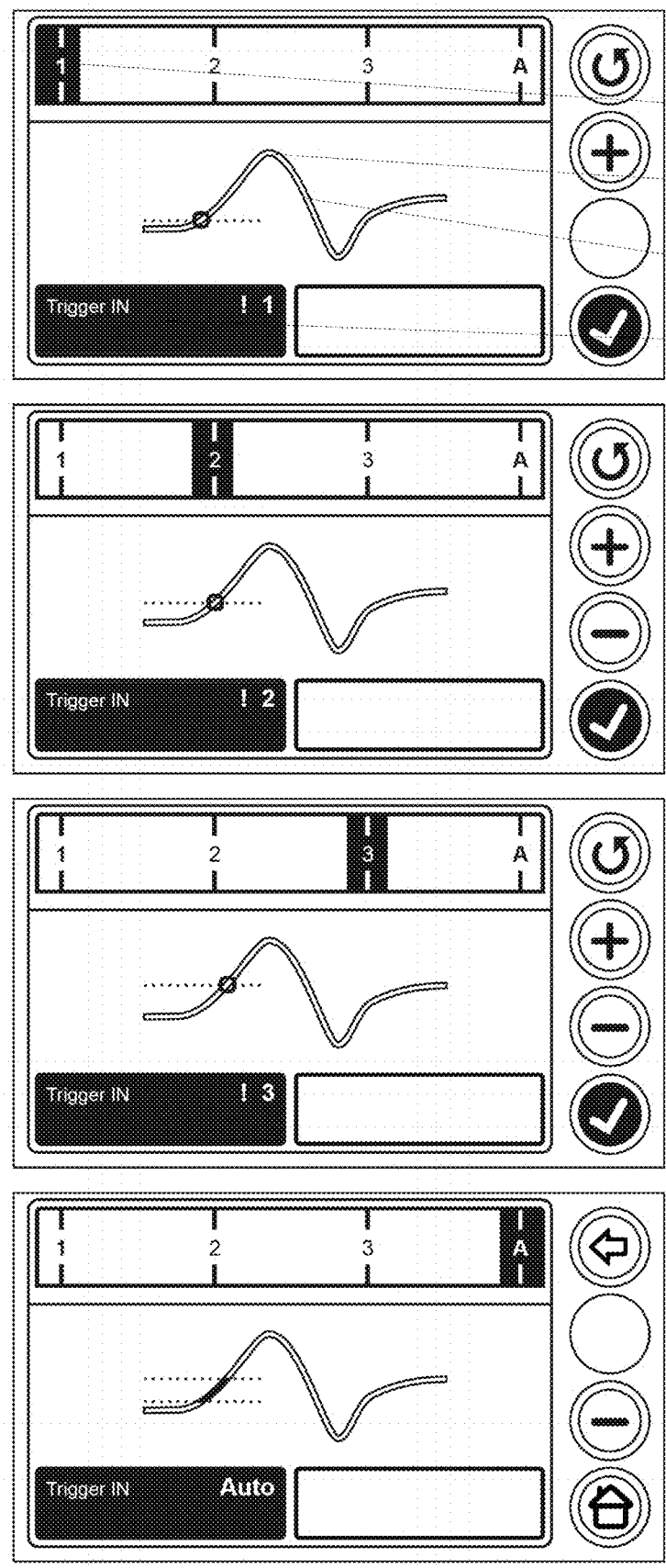
FIG. 8 shows a schematic illustration of a graphical adjustment aid for the trigger sensitivity.

In a similar manner to FIG. 7, FIG. 8 shows the adjustment of the trigger sensitivity (40). The threshold value (41) is schematically illustrated in the figure as a green line. In comparison with FIG. 7, it is seen that values which do not represent a numerical value can also be selected in the slider/ruler, in this case "A" for the auto level. The operating device for a breathing apparatus comprises a touch-sensitive graphical display (3, 13, 14, 15), which at least occasionally represents the range of values for a breathing parameter (14a . . . 14x), here the trigger sensitivity (40), and numerically displays (42) at least individual values of the trigger sensitivity, and a memory (21) for the value of the trigger sensitivity of at least one data point associated with the range of values. At least one position (14a . . . 14x) on the touch-sensitive graphical display which is associated with the data point using switching logic and switching logic (18) which, when the position on the touch-sensitive graphical display which is associated with the data point using switching logic is touched, causes at least one numerical value (32) associated with the data point and/or a confirmation field (33) for the numerical value to be displayed are likewise used. Switching logic (18) which, when the numerical value (32) or the confirmation field (33) is touched, applies this numerical value to the associated respiratory gas parameter and writes this numerical value, with the associated respiratory gas parameter, to the memory (21) is likewise provided.

The operating field is in the form of a number line or ruler and the entire range of values is visualized on the display (13) in the form of a number line or bar and the visualized number line is also in the form of an operating field (14f). The operating field is touch-sensitive over the entire visualized adjustment range and the desired value can be selected by only touching the desired range. Finger pressure or touching inside the ruler is evaluated with respect to its position in such a manner that it is not necessary to strike precisely one of the numbers 1, 2, 3, but rather the finger pressure is assigned to the closest number. The detected value (32) is visualized in an additional field (14/1).

The detected value can be additionally adjusted using the symbols +/− (14/2, 14/3). Not only individual values of the trigger sensitivity are preferably numerically displayed (42), but the selected value of the trigger sensitivity is also numerically displayed (43) and the selected trigger sensitivity is also graphically visualized (41). Three fixed trigger levels are provided in the present case. However, they may also be adjusted using the symbols +/− (14/2, 14/3) in order to thus fine-tune the trigger on a patient-specific basis. If the level "A" is selected for the auto level, the trigger is adaptively adjusted within predefined limit values which are also graphically visualized.

FIG. 9 shows the graphical adjustment aid for at least one inspiratory pressure and one expiratory pressure. The position of the pressure tile below the graph illustrates which is the inspiratory pressure and which is the expiratory pressure, and that PDIFF is the pressure swing (54). The color of the tiles represents:
  green: currently selected parameter which can be adjusted using a slider or +/− keys
  gray: parameter which can alternatively be selected for adjustment
  black: informatively displayed parameter which is produced as a consequence of the adjustments.

Alternatively, not only the value of the parameter to be currently adjusted could be displayed in the slider in one color, but rather the values of further parameters could be additionally displayed using a marking which differs in terms of shape and/or color. The operating device for a breathing apparatus comprises a touch-sensitive graphical display (3, 13, 14, 15), which at least occasionally represents the range of values for a breathing parameter (14a . . . 14x), here the IPAP and/or EPAP and/or EEPAP pressure values (50), and numerically displays (51) at least individual values of the trigger sensitivity, a memory (21) for the pressure value, at least one data point associated with the range of values, at least one position (14a . . . 14x) on the touch-sensitive graphical display which is associated with the data point using switching logic, switching logic (18) which, when the position on the touch-sensitive graphical display which is associated with the data point using switching logic is touched, causes at least one numerical value (52) associated with the data point and/or a confirmation field for the numerical value to be displayed, and switching logic (18) which, when the numerical value (52) or the confirmation field is touched, applies this numerical value to the associated respiratory gas parameter and writes this numerical value, with the associated respiratory gas parameter, to the memory (21).

The operating field is in the form of a number line or ruler and the entire range of values is visualized on the display (13) in the form of a number line or bar and the visualized number line is also in the form of an operating field (14/). The operating field is touch-sensitive over the entire visualized adjustment range and the desired value can be selected by only touching the desired range. Finger pressure or touching within the ruler is evaluated with respect to its position in such a manner that it is not necessary to strike precisely one of the numbers, but rather the finger pressure is assigned to the closest number. The detected value (52) is visualized in an additional field (14/1).

The detected value can be additionally adjusted using the symbols +/− (14/2, 14/3). Not only are individual pressure values preferably numerically displayed (52), but the selected value is also numerically displayed and the selected pressure is also graphically visualized (53). However, the latter can also be adjusted using the symbols +/− (14/2, 14/3). The resulting pressure swing is preferably also displayed as a numerical value (55) and graphically visualized (54) for information.

Figure 10:
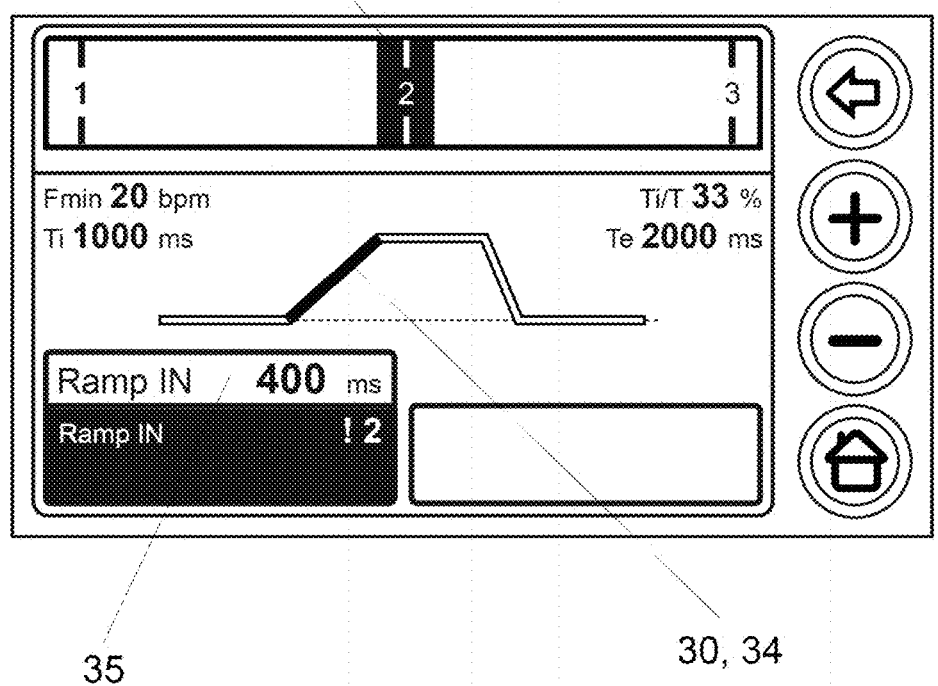
FIG. 10 shows an additional illustration for FIG. 7.

As an addition to FIG. 7 and in combination with the instantaneous ramp gradient 1, 2 or 3 (31), the adjustment of further parameters logically connected thereto is also informatively displayed according to FIG. 10. As a result, the user can usefully select the value to be currently adjusted without having to keep in mind all of the other parameters. As a consequence of the instantaneous ramp gradient and the other parameters, the currently valid ramp time in ms (35) is calculated and is likewise informatively displayed.

Figure 11:
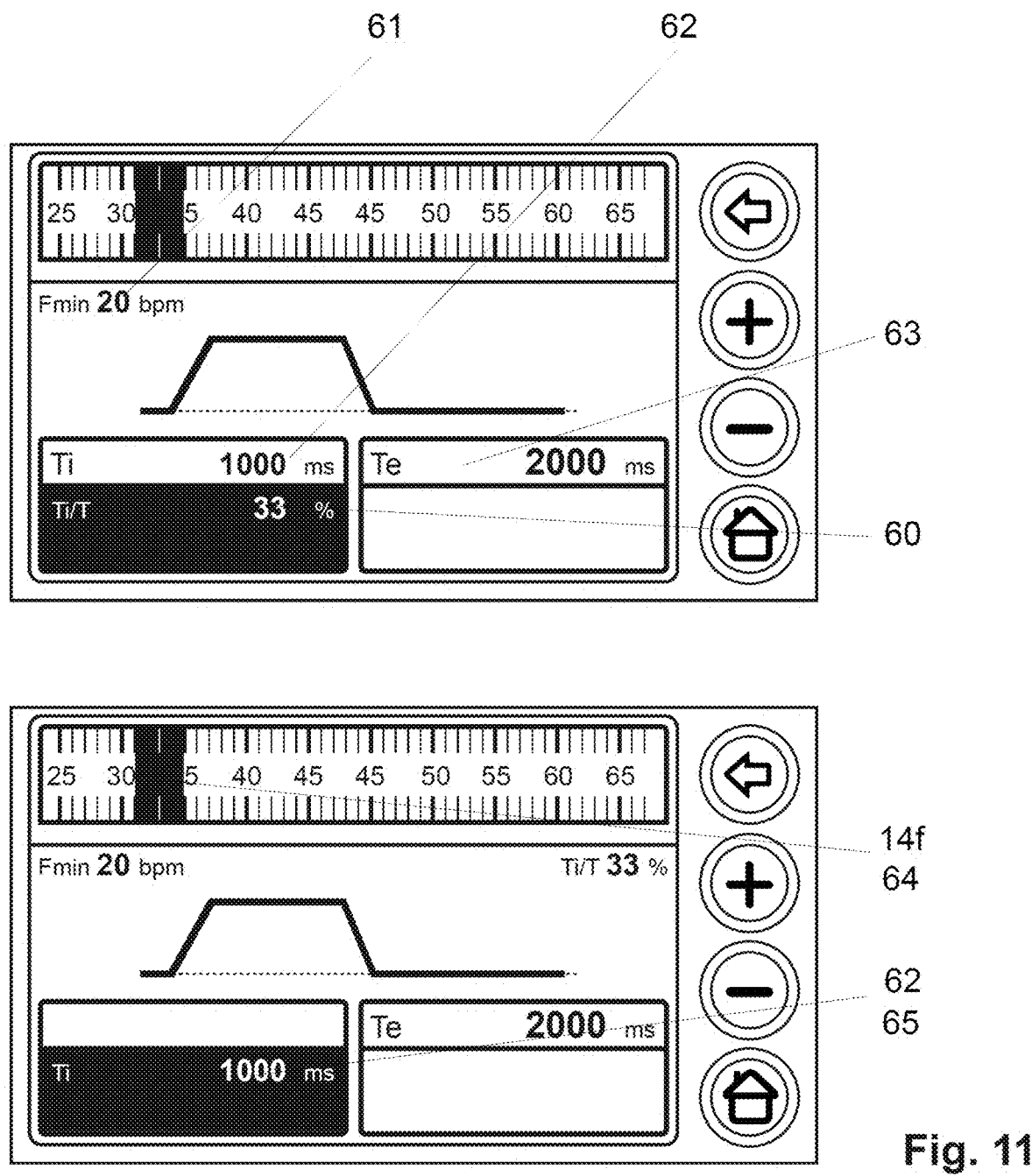
FIG. 11 shows an image for illustrating a ratio of inspiratory time and the total breathing time.

FIG. 11 shows the adjustment of the ratio of inspiratory time to the total breathing time in % (60). The selected breathing frequency (61) is additionally displayed. As a consequence of the adjusted breathing frequency and the adjusted ratio Ti/T, the inspiratory period Ti (62) and expiratory period Te (62) are calculated and informatively displayed.

The lower half illustrates an alternative embodiment in which the inspiratory period is adjusted, and the expiratory period and Tiff automatically result therefrom in combination with the selected breathing frequency. The operating device for a breathing apparatus comprises a touch-sensitive graphical display (3, 13, 14, 15), which at least occasionally represents the range of values for a breathing parameter (14a . . . 14x), here the inspiration period (62), and numerically displays (64) at least individual values, a memory (21) for the inspiratory period, at least one data point associated with the range of values, at least one position (14a . . . 14x) on the touch-sensitive graphical display which is associated with the data point using switching logic, switching logic (18) which, when the position on the touch-sensitive graphical display which is associated with the data point using switching logic is touched, causes at least one numerical value (65) associated with the data point and/or a confirmation field for the numerical value to be displayed, and switching logic (18) which, when the numerical value (65) or the confirmation field is touched, applies this numerical value to the associated respiratory gas parameter and writes this numerical value, with the associated respiratory gas parameter, to the memory (21).

The operating field is in the form of a number line or ruler and the entire range of values is visualized on the display (13) in the form of a number line or bar and the visualized number line is also in the form of an operating field (14/). The operating field is touch-sensitive over the entire visualized adjustment range and the desired value can be selected by only touching the desired range.

Finger pressure or touching within the ruler is evaluated with respect to its position in such a manner that it is not necessary to strike precisely one of the numbers, but rather the finger pressure is assigned to the closest number. The detected value (52) is visualized in an additional field (14/1). The detected value can be additionally adjusted using the symbols +/− (14/2, 14/3). Not only are individual values preferably numerically displayed, but the selected value is also numerically displayed and the selected value is also graphically visualized. However, the latter can also be adjusted using the symbols +/− (14/2, 14/3). The resulting exhalation time (63) is preferably also displayed as a numerical value (63) and/or graphically visualized for information.

FIG. 12 shows the described circular embodiment of the operating element. A dial which can be operated using a finger is simulated on a touch-sensitive display. A display element which is likewise circular and displays at least the currently set value—19 minutes in the example—particularly preferably also the value limits or the range of values—0 to 45 minutes in the example—is placed around the operating field. The display is effected as a number and additionally particularly preferably by means of a colored and/or thicker marking (74) which represents the instantaneous values in relation to the entire range of values.

The operating device for a breathing apparatus comprises a touch-sensitive graphical display (3, 13, 14, 15), which at least occasionally represents the range of values for a breathing parameter (14a . . . 14x) and numerically displays (71) at least individual values, a memory (21) for at least one data point associated with the range of values, at least one position (14a . . . 14x) on the touch-sensitive graphical display which is associated with the data point using switching logic, switching logic (18) which, when the position on the touch-sensitive graphical display which is associated with the data point using switching logic is touched, causes at least one numerical value (71) associated with the data point and/or a confirmation field for the numerical value to be displayed, and switching logic (18) which, when the numerical value (71) or the confirmation field is touched, applies this numerical value to the associated respiratory gas parameter and writes this numerical value, with the associated respiratory gas parameter, to the memory (21).

The operating field is in the form of a rotary knob or a dial (73) and the entire range of values or a partial range of values is visualized on the display (13) in the form of a numerical ring (72) and the visualized numerical ring is also in the form of an operating field (14/). The operating field is touch-sensitive over the entire visualized adjustment range and the desired value can be selected by only touching the desired range. Finger pressure or touching within the numerical ring is evaluated with respect to its position in such a manner that it is not necessary to strike precisely one of the numbers, but rather the finger pressure is assigned to the closest number.

Alternatively, swiping over the numerical ring is detected as an adjustment process and stopping of the swiping movement is detected as a selection. That value which is detected when the movement is stopped—the detected value (71)—is visualized in an additional field (14/1). The detected value can be additionally adjusted using the symbols +/− (14/2, 14/3). Not only are individual values preferably numerically displayed, but the selected value is also numerically displayed and the selected value is also graphically visualized. However, the latter can also be adjusted using the symbols +/− (14/2, 14/3).

The parameter (75) to be currently adjusted is particularly preferably displayed with its name and/or an internationally comprehensible symbol (75) and/or its unit (75). In the example illustrated, the parameter could be the ramp time as a sleeping aid of a therapy apparatus, which is displayed in minutes. Alternatively, therapy pressures or the power levels of a respiratory humidifier, inter alia, can be displayed and adjusted.

If the user carries out a rotational movement on the displayed dial using a finger, preferably in the clockwise direction, the selected value is increased, from 19 to 32 minutes in the example. A rotational movement in the opposite direction results in a reduction in the selected value. If the intended value is reached, it can be accepted and used by the apparatus. This is typically carried out either after expiry of a waiting time without further adjustment or after pressing a confirmation key/confirmation area (76) which is indicated, for example, with "accept", "ok", "use", a check symbol or the like. This is particularly preferably situated in the center of the displayed dial.

Figure 13:
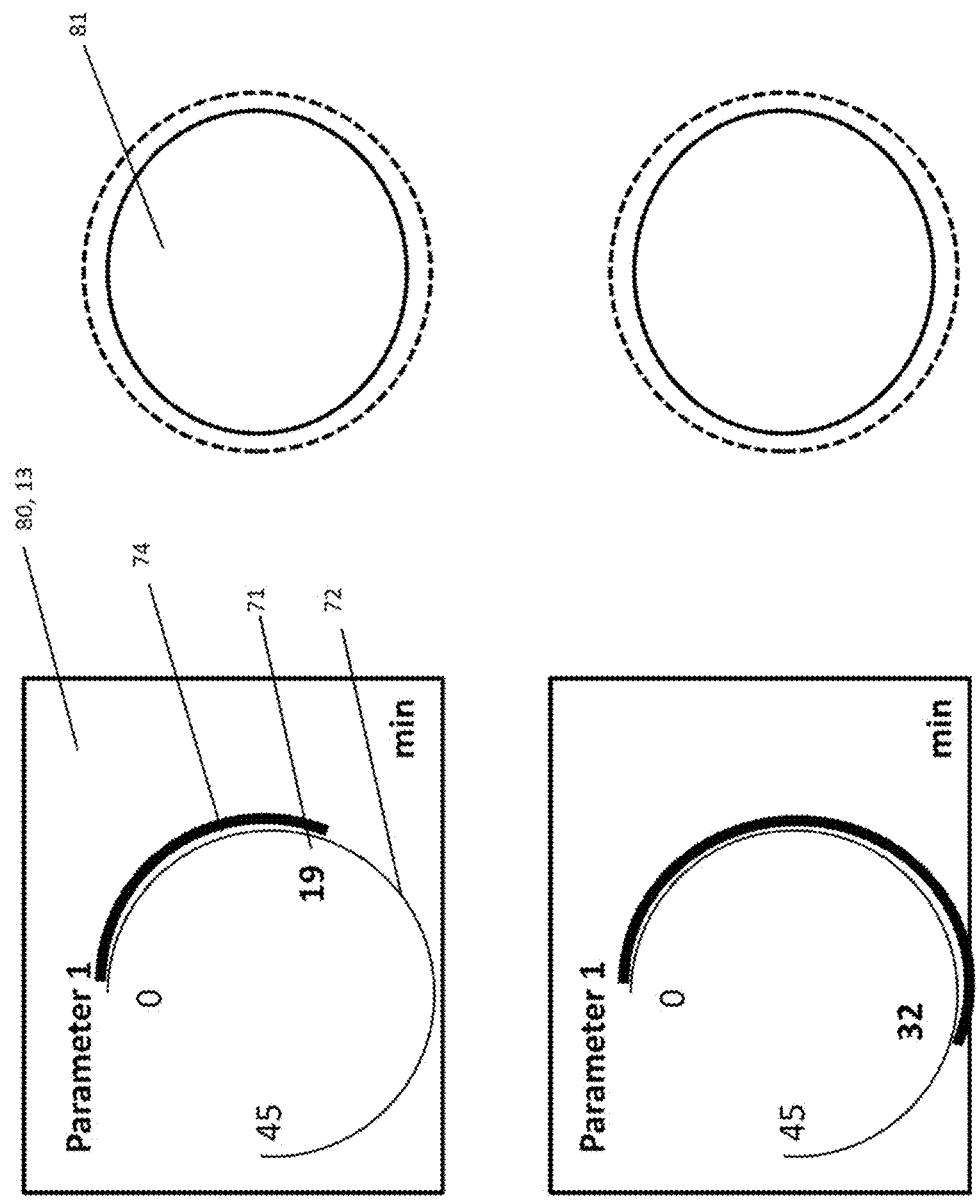
FIG. 13 shows an embodiment wherein the "dial" operating element and the circular display element are situated beside one another or below one another.

FIG. 13 shows an alternative embodiment. In this case, the "dial" operating element and the circular display element are situated beside one another or below one another. This is a preferred embodiment if a touch-sensitive display element is not used, but rather only a graphical display element (80) having a separate mechanical rotary pushbutton (81). This embodiment provides an advantage since the mechanical rotary pushbutton (81) can preferably be used for fine adjustments owing to the haptics or better operability. The graphical visualization of the adjustment process and/or of the selected value and/or of the available range of values, which is decoupled from the mechanical rotary pushbutton (81), provides the advantage that a larger and improved display can be selected than could be provided by a scale beside the mechanical rotary pushbutton (81).

In this case, a selected value is particularly preferably confirmed by pressing the rotary pushbutton (81).

Otherwise, the type of display and adjustment is comparable with the exemplary embodiment in FIG. 12, which is why the description with respect to FIG. 12 can also be used for the example in FIG. 13.

According to the invention, a (start/stop) operating area (14x) can be provided on the touchscreen or a mechanical (start/stop) operating element (2) according to FIG. 14 can be provided, the actuation of which causes the operating and information system (3) to start or stop the ventilation via the control unit.

The invention provides for the (start/stop) operating area (14x) on the touchscreen to have a different form depending on the situation; for example, if the ventilation is not active but can be started, the (start/stop) operating area (14x) on the touchscreen at least partially has a green color, for example, or has a start symbol and additionally has an item of written information "start ventilation", for example. If the ventilation is active and can be stopped, the (start/stop) operating area (14x) on the touchscreen at least partially has a red color or has a stop symbol and additionally has an item of written information "stop ventilation", for example.

In this case, provision is made, for example, for the (start/stop) operating area (14x) to otherwise appear unchanged always at the same position on the touchscreen and/or always in the same size.

If the (start/stop) operating area (14x) on the touchscreen for stopping the ventilation "stop ventilation" is confirmed, instantaneous settings for the ventilation, for example instantaneous pressure values, are stored by the control unit in a retrievable manner and are read out again in response to actuation of the (start/stop) operating area (14x) again—for starting the ventilation—and are activated for the ventilation, in particular provided that no changes were made to the ventilation settings while ventilation was stopped.

What is claimed is:

1. An operating and information system for a breathing apparatus, wherein the system comprises a display for displaying information and for displaying operating fields for a user and having at least one touch-sensitive input field in spatial proximity to a displayed operating field and wherein
a first operating field and a second operating field are displayed in a region of the display, and
a processing unit which is coupled to the display and to the touch-sensitive input unit is configured
to detect operation of the first operating field via the touch-sensitive input unit and, on the basis thereof, to cause a control unit to carry out or display a function assigned to the operating field, and wherein the control unit registers current or resistance or voltage changes in a region of interfaces or connections to a humidifier and thereby detects when a humidifier is adapted to a humidifier connection, and the control unit then displays a new menu with an operating field for the humidifier via the display.

2. The system of claim 1, wherein operation of the second operating field is detected by the processing unit via a touch-sensitive input unit and the control unit is then caused to call up a context-dependent submenu, the submenu comprising a selection of actuatable adjustment functions for the menu, the control unit visualizing adjusted parameters in a region of the menu and applying them by control commands to an associated actuator.

3. The system of claim 1, wherein a memory is assigned to the control unit and adjusted parameters or values are written to the memory by the control unit, the memory storing at least the values input and/or used last.

4. The system of claim 1, wherein an undo function is provided and an undo operating field is provided for an undo function, and touching of the undo operating field is detected by the processing unit coupled to a touch-sensitive input unit, and the processing unit then causes the control unit to retrieve the values stored last from a memory and to visualize or use them.

5. The system of claim 1, wherein operating processes and/or apparatus outputs are prioritized by the control unit and this is carried out automatically by the control unit in accordance with stored rules in such a manner that, if the control unit registers an operating process with a higher priority or an apparatus output, it at least partially superimposes the operating process with the higher priority or the apparatus outputs on an instantaneous operating field in a region of the display.

6. The system of claim 1, wherein the display is lit or backlit and is controlled by the control unit in such a manner that, after a defined or definable period in which a touch-sensitive input unit is not used (no touching), the control unit automatically dims the lit or backlit display or completely switches off the lighting or backlighting and/or wherein touching of the touch-sensitive input unit is transmitted to the control unit by the processing unit in a state of dimmed lighting or backlighting or lighting or backlighting which has been completely switched off, and the control unit then lights or backlights the display again.

7. The system of claim 1, wherein the control unit detects storage media connected via an interface and displays a connected storage medium as an operating field in a region of a touch-sensitive input unit and data which are extraneous to a therapy are therefore also loaded into the breathing apparatus and/or executed by the latter.

8. The system of claim 1, wherein a menu for controlling the humidifier is displayed substantially at a position on the display which was previously not occupied by a menu.

9. The system of claim 1, wherein additional operating fields which are initially not active are visualized adjacent to the operating field, actuation of the operating field being detected by the processing unit which causes the control unit to activate the operating fields, and the latter being used to adjust a humidifier heating level, a selected humidifier level then being displayed in the operating field, and the selected value also being adjusted and used by the control unit by a control signal to the humidifier.

10. An operating and information system for a breathing apparatus, wherein the system comprises a display for displaying information and for displaying operating fields for a user and having at least one touch-sensitive input field in spatial proximity to a displayed operating field and wherein
a first operating field and a second operating field are displayed in a region of the display, and
a processing unit which is coupled to the display and to the touch-sensitive input unit is configured
to detect operation of the first operating field via the touch-sensitive input unit and, on the basis thereof, to cause a control unit to carry out or display a function assigned to the operating field, and wherein the control unit registers current or resistance or voltage changes in a region of a heating element of a humidifier and thereby detects a falling or low water level on the basis of an increased current or resistance or voltage value of the heating element and this causes the control unit to display a symbol or a text message symbolizing or mentioning a low water level in the region of the display.

11. The system of claim 1, wherein a start/stop operating area is present.

12. The system of claim 1, wherein individual values of a breathing parameter are numerically displayed and a selected value is also numerically displayed and a selected breathing parameter is also graphically visualized.

13. The system of claim 1, wherein three fixed levels are provided for a breathing parameter and these levels can be adjusted using the symbols +/− to thereby fine-tune the breathing parameter on a patient-specific basis.

14. The system of claim 10, wherein operation of the second operating field is detected by the processing unit via a touch-sensitive input unit and the control unit is then caused to call up a context-dependent submenu, the submenu comprising a selection of actuatable adjustment functions for the menu, the control unit visualizing adjusted parameters in a region of the menu and applying them by control commands to an associated actuator.

15. The system of claim 10, wherein a memory is assigned to the control unit and adjusted parameters or values are written to the memory by the control unit, the memory storing at least the values input and/or used last.

16. The system of claim 10, wherein an undo function is provided and an undo operating field is provided for an undo function, and touching of the undo operating field is detected by the processing unit coupled to a touch-sensitive input unit, and the processing unit then causes the control unit to retrieve the values stored last from a memory and to visualize or use them.

17. The system of claim 10, wherein operating processes and/or apparatus outputs are prioritized by the control unit and this is carried out automatically by the control unit in accordance with stored rules in such a manner that, if the control unit registers an operating process with a higher priority or an apparatus output, it at least partially superimposes the operating process with the higher priority or the apparatus outputs on an instantaneous operating field in a region of the display.

18. The system of claim 10, wherein the display is lit or backlit and is controlled by the control unit in such a manner that, after a defined or definable period in which a touch-sensitive input unit is not used (no touching), the control unit automatically dims the lit or backlit display or completely switches off the lighting or backlighting and/or wherein touching of the touch-sensitive input unit is transmitted to the control unit by the processing unit in a state of dimmed lighting or backlighting or lighting or backlighting which has been completely switched off, and the control unit then lights or backlights the display again.

19. The system of claim 10, wherein individual values of a breathing parameter are numerically displayed and a selected value is also numerically displayed and a selected breathing parameter is also graphically visualized.

20. The system of claim 10, wherein three fixed levels are provided for a breathing parameter and these levels can be adjusted using the symbols +/− to thereby fine-tune the breathing parameter on a patient-specific basis.

* * * * *